US00PP33280P2

(12) United States Plant Patent
van Langen

(10) Patent No.: US PP33,280 P2
(45) Date of Patent: Jul. 20, 2021

(54) *PACHYVERIA* PLANT NAMED 'AMIECH1621'

(50) Latin Name: ***Echeveria hookeri* x *Pachyphytum oviferum* x *Pachyveria***
Varietal Denomination: AMIECH1621

(71) Applicant: NovoAmi B. V., Heerhugowaard (NL)

(72) Inventor: Gerard van Langen, Heerhugowaard (NL)

(73) Assignee: NovoAmi B. V., Heerhugowaard (NL)

( * ) Notice: Subject to any disclaimer, the term of this patent is extended or adjusted under 35 U.S.C. 154(b) by 0 days.

(21) Appl. No.: 16/895,254

(22) Filed: Jun. 8, 2020

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
CPC ... A01H 5/12; A01H 5/02; A01H 5/00; A01H 6/32; A01H 6/00
See application file for complete search history.

(56) References Cited

PUBLICATIONS

Upov Pluto Plant Variety Database Nov. 4, 2020 for *Pachyveria* Amiech1621, retrieved on Nov. 9, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — Samuel R. McCoy, Jr.

(57) ABSTRACT

A new and distinct *Pachyveria* hybrid plant named 'AMIECH1621' which is characterized by light greyed-green, durable foliage that is tightly held in a compact basal rosette and the stability of these characteristics from generation to generation.

4 Drawing Sheets

Latin name of the genus and species: The Latin name of the genus and species of the novel variety disclosed herein is *Echeveria hookeri* x *Pachyphytum oviferum* which is also known by the nothogenus, x *Pachyveria*.

Variety denomination: The inventive variety of *Pachyveria* hybrid disclosed herein has been given the variety denomination 'AMIECH1621'.

BACKGROUND OF THE INVENTION

Parentage: 'AMIECH1621' is an intergeneric hybrid seedling selection resulting from the controlled pollination of an unnamed *Echeveria hookeri* plant (not patented), the seed parent, with an unnamed *Pachyphytum oviferum* plant (not patented), the pollen parent. The crossing was made by the inventor in the spring of 2013 at a commercial greenhouse in Heerhugowaard, the Netherlands. In autumn of 2014, one seedling was observed which exhibited unique growth and foliage characteristics. The seedling was isolated for further evaluation in order to confirm the distinctness and stability of the characteristics first observed. Upon confirmation of distinctness and stability, 'AMIECH1621' was selected for commercialization.

Asexual Reproduction: Asexual reproduction of the new cultivar 'AMIECH1621', by way of rooting leaf cuttings, was first initiated in the spring of 2015 at the inventor's commercial greenhouse in Heerhugowaard, the Netherlands. Through six subsequent generations, the unique features of this cultivar have proven to be stable and true to type.

SUMMARY OF THE INVENTION

The cultivar 'AMIECH1621' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1621'. These characteristics in combination distinguish 'AMIECH1621' as a new and distinct *Pachyveria* hybrid cultivar:

1. 'AMIECH1621' exhibits narrow obovate foliage tightly held in a compact basal rosette; and
2. 'AMIECH1621' exhibits yellow-green to greyed-green foliage that is moderately covered with lighter greyed-green epicuticular wax; and
3. 'AMIECH1621' foliage which is very durable.

BOTANICAL DESCRIPTION OF THE PLANT

Figure 1:
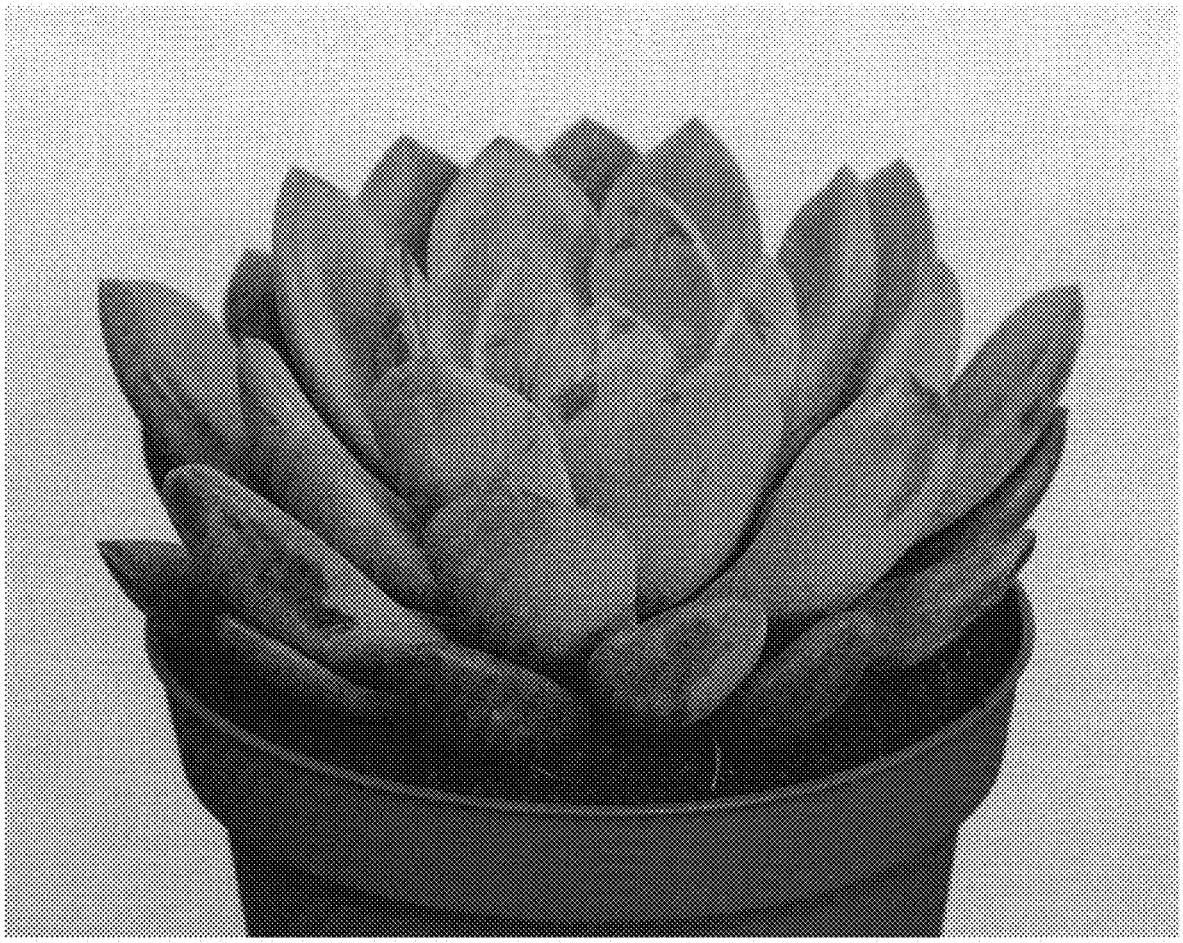
FIG. 1 illustrates, as nearly true as it is reasonably possible to make the same in color photographs of this type, an exemplary plant of 'AMIECH1621' grown in a commercial greenhouse in Heerhugowaard, the Netherlands. This plant is approximately 8 months old, shown planted in an 11 cm container.
Figure 2:
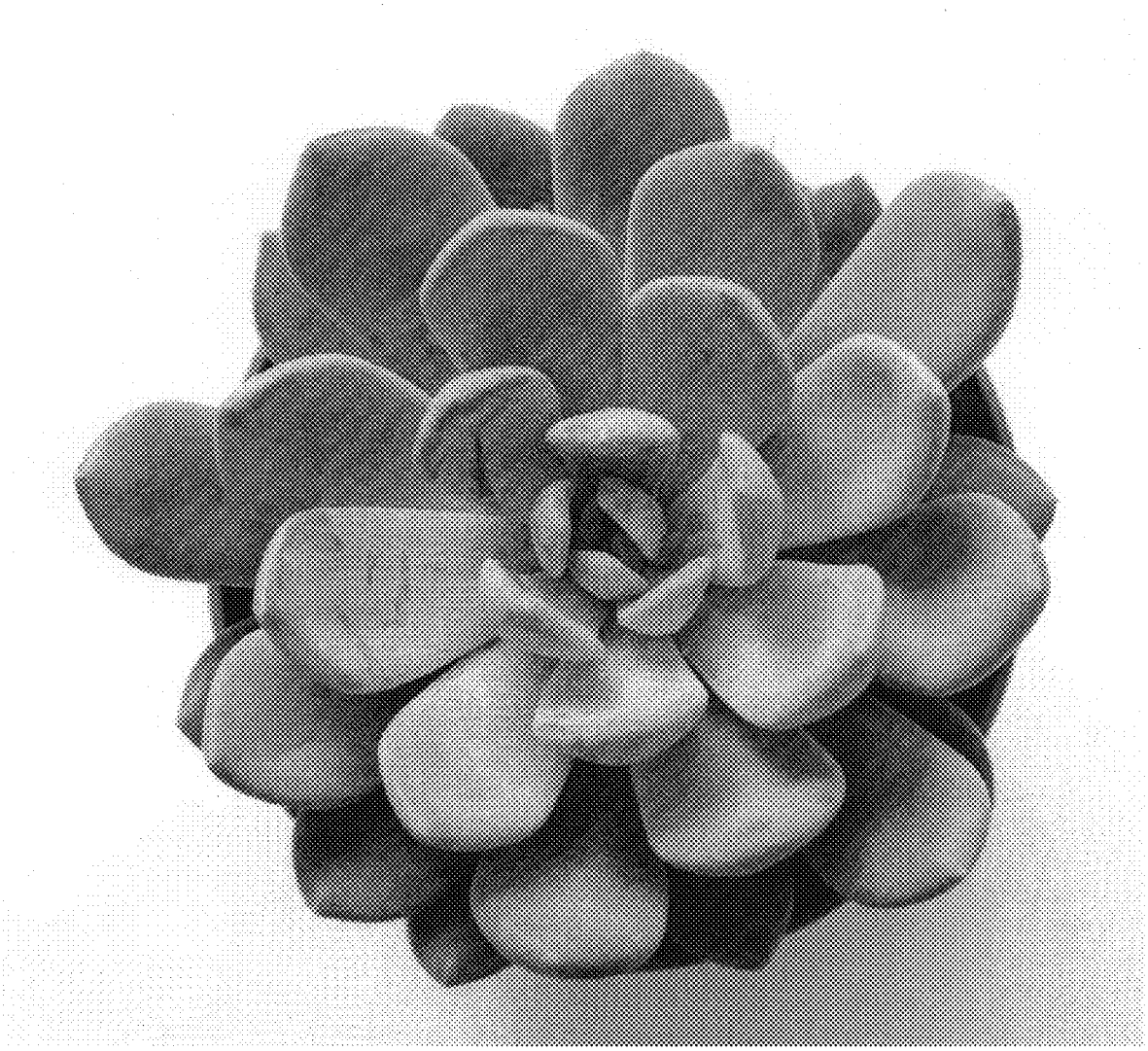
FIG. 2 illustrates, as nearly true as it is reasonably possible to make the same in color photographs of this type, the typical foliage arrangement of 'AMIECH1621'.
Figure 3:
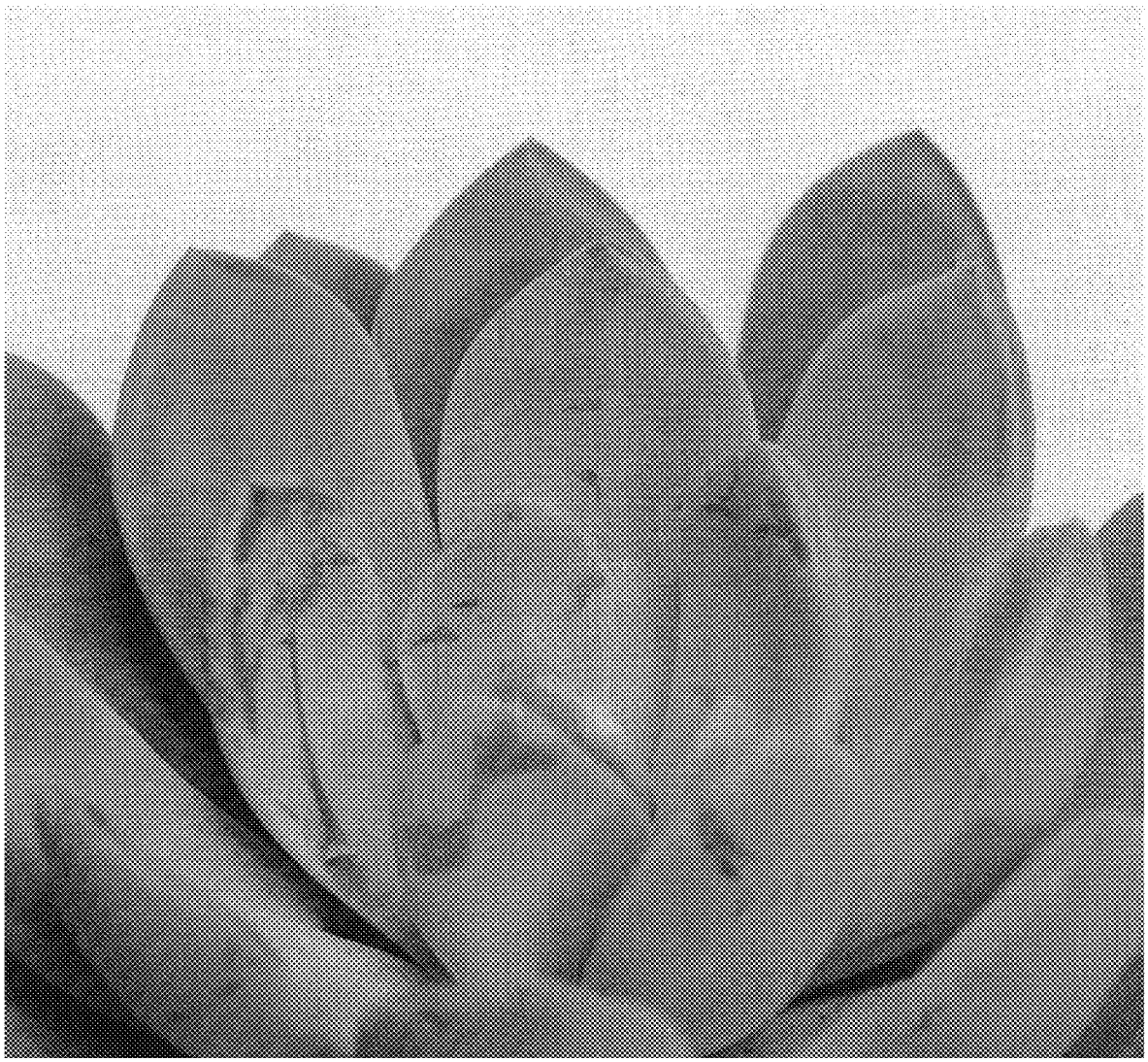
FIG. 3 illustrates, as nearly true as it is reasonably possible to make the same in color photographs of this type, the adaxial surface of the mature foliage 'AMIECH1621'.
Figure 4:
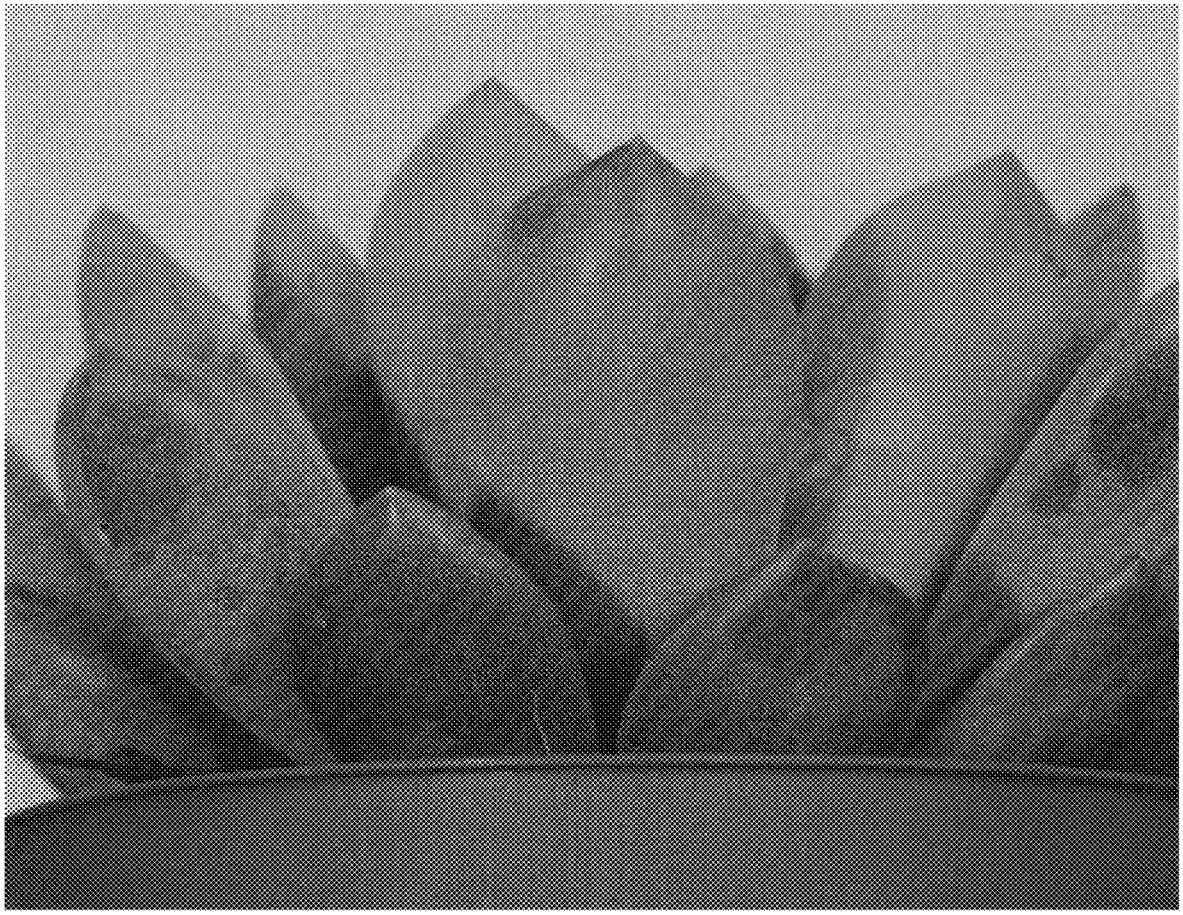
FIG. 4 illustrates, as nearly true as it is reasonably possible to make the same in color photographs of this type, the abaxial surface of the mature foliage 'AMIECH1621'.

The following observations and measurements made in January of 2020 describe averages from a sample set of six specimens of 8 months old 'AMIECH1621' plants grown in 11 cm nursery containers at commercial greenhouse in Heerhugowaard, the Netherlands. Plants were produced using conventional greenhouse production protocols for *Pachyveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1621' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1621' and comparisons with the parent plants and closest known comparator are provided below.

Plant description:

*Growth habit*.—Succulent perennial with foliage growing in a non-branched basal rosette.

*Plant shape*.—Flattened to flattened globular.

*Height from soil level to top of foliar plane*.—5.7 cm.

*Plant spread*.—Average of 11.3 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 7 cm container.

*Disease and pest resistance or susceptibility*.—Neither resistance nor susceptibility to typical *Pachyveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 38 leaves per rosette.

*Shape*.—Narrow obovate.

*Dimensions*.—6.5 cm long, 2.3 cm wide, and 1.0 cm thick, on average.

*Aspect*.—Slightly concave and slightly curved upward.

*Attitude*.—Juvenile foliage at the center of the rosette is held upward; foliage becomes progressively more relaxed towards the outer whorls of mature foliage, at an average angle of 50 degrees from horizontal.

*Apex*.—Broad acute to apiculate.

*Base*.—Cuneate.

*Margin*.—Entire except near the apex which is very slightly crenate to sinuate; not undulated or lobed.

*Pubescence, texture and luster of the adaxial surface*.—Glabrous, smooth, and matte; moderately glaucous.

*Pubescence, texture and luster of the abaxial surface*.—Glabrous, smooth, and matte; moderately glaucous.

*Color*.—Juvenile foliage, adaxial surface — Greyed-green, nearest to RHS 191B; margined lighter, nearest to RHS 192B; the epicuticular glaucous wax covering the leaf surface is greyed-green, nearest to a mixture of RHS 188A and 188B. Juvenile foliage, abaxial surface — Greyed-green, nearest to a mixture of RHS 194A and 194B; margined lighter, nearest to RHS 192B; the epicuticular glaucous wax covering the leaf surface is greyed-green, nearest to a mixture of RHS 188A and 188B. Mature foliage, adaxial surface — Nearest to in between yellow-green and greyed-green, RHS 148A and 191A, and fading to greyed-green towards the base, nearest to RHS 194B; margined slightly darker towards the apex, nearest to RHS 195A; the epicuticular glaucous wax covering the leaf surface is greyed-green, nearest to a mixture of RHS 188A and 188B. Mature foliage, abaxial surface — Nearest to in between yellow-green and greyed-green, RHS 148A and 191A, and fading to greyed-green towards the base, nearest to RHS 194B; margined slightly darker towards the apex, nearest to RHS 195A; the epicuticular glaucous wax covering the leaf surface is greyed-green, nearest to a mixture of RHS 188A and 188B. Venation — No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIECH1621' differ from the seed parent, an unnamed *Echeveria hookeri* plant (not patented), in the following characteristics described in Table 1 below.

TABLE 1

| Characteristic | 'AMIECH1621' | The seed parent. |
|---|---|---|
| Foliage thickness. | More flattened when compared to the parent. | More rounded when compared to 'AMIECH1621'. |
| General coloration of the foliage. | Light greyed-green. | Light blue-green. |
| Color pattern on the foliage. | No patterning. | Marbled. |

Plants of the new cultivar 'AMIECH1621' differ from the pollen parent, an unnamed *Pachyphytum oviferum* plant (not patented), in the following characteristics described in Table 2 below.

TABLE 2

| Characteristic | 'AMIECH1621' | The pollen parent. |
|---|---|---|
| Growth habit. | Foliage is more tightly held in basal rosette. | Foliage is more loosely held in a basal rosette. |

TABLE 2-continued

| Characteristic | 'AMIECH1621' | The pollen parent. |
|---|---|---|
| Foliage aspect. | More flattened when compared to the parent. | More rounded when compared to 'AMIECH1621'. |
| Foliage length. | Longer than the parent. | Shorter than 'AMIECH1621'. |
| General coloration of the foliage. | Light greyed-green. | Light purple, suffused with pink. |

COMPARISONS WITH THE CLOSEST KNOWN COMPARATOR

Plants of the new cultivar 'AMIECH1621' differ from the closest known commercial comparator, *Pachypythum* hybrid 'Corvus' (abandoned U.S. Plant patent application Ser. No. 14/756,347), in the following characteristics described in Table 3 below.

TABLE 3

| Characteristic | 'AMIECH1621' | 'Corvus' |
|---|---|---|
| Foliage shape. | Narrow obovate. | Oblanceolate. |
| Foliage glaucescence. | Moderately glaucous. | Heavily glaucous. |
| General coloration of the foliage. | Light greyed-green. | Light blue-green. |

That which is claimed is:

1. A new and distinct variety of *Echeveria hookeri* x *Pachyphytum oviferum* hybrid plant named 'AMIECH1621', substantially as described and illustrated herein.

* * * * *